United States Patent
Parrott

(10) Patent No.: US 6,461,830 B1
(45) Date of Patent: Oct. 8, 2002

(54) DETERMINING EXISTENCE OF PREECLAMPSIA IN PREGNANCIES BY MEASURING LEVELS OF GLYCEROPHOSPHATIDYL COMPOUNDS, GLYCEROPHOSPHATIDYCHOLINE, LYSOPHOSPHOLIPIDS AND LYSOPHOSPHATIDYLCHOLINE

(75) Inventor: Jeff A. Parrott, Irvine, CA (US)

(73) Assignee: Atairgin Technologies, Inc., Irvine, CA (US)

( * ) Notice: Subject to any disclaimer, the term of this patent is extended or adjusted under 35 U.S.C. 154(b) by 0 days.

(21) Appl. No.: 09/585,138

(22) Filed: Jun. 1, 2000

(51) Int. Cl.$^7$ .............................. C12Q 1/44; C12Q 1/26; C12Q 1/32; C12N 9/20

(52) U.S. Cl. ............................. 435/19; 435/25; 435/26; 435/198; 436/164

(58) Field of Search ............................ 435/198, 19, 25, 435/26; 436/65

(56) References Cited

U.S. PATENT DOCUMENTS 6,225,063 B1 * 7/2001 Small et al.

OTHER PUBLICATIONS

Endressen et al. (1993). Increased lipolytic activity of sera of pre-eclamptic women due to the presence of a lysophospholipase. Scand J Clin Lab Invest 53(7), pp 733–739.*

A Discriminant Function for Preeclampsia: Case–Control Study of Minor Hemoglobins, Red Cell Enzymes, and Clinical Laboratory Values, Braun, K, et al., Am. J. of Perinatology, 1999, 14:297–302.

Pre–eclampsia and the HELLP syndrome still cause maternal mortality in the Netherlands and other developed countries; can we reduce it?, Onrust, S., et al., Euro. J. of Obstet. Gynecol. and Reproductive Biol. 1999;82:41–46.

Preeclampsia Is Associated with Widespread Apoptosis of Placental Cytotrophoblasts within the uterine Wall, DiFederico, E., et al., Am. J. Pathol. 1999;155:293–301.

Preeclampsia Is Associated with Abnormal Expression of Adhesion Molecules by Invasive Cytotrophoblasts, Zhou,Y., et al., J. Clin. Invest., 1993;91:950–960.

Circulating Levels of Immunoreactive Cytokine in Women with Preeclampsia, Conrad, K., et al., AJRI 1998; 40:102–111.

Eicosanoid secretion by human endothelial cells exposed to normal pregnancy and preeclampsia plasma in vitro, de Groot, C., et al., Prostaglandins, Leukotrienes and Essential Fatty Acids (1998) 58(2), 91–97.

Etiology and pathogenesis of preeclampsia: Current concepts, Dekker, G., et al., Am. J. Obstet Gynecol 1998; 179:1359–75.

Fasting serum triglycerides, free fatty acids, and malondialdehyde are increased in preeclampsia, are positively correlated, and decrease within 48 hours post partum, Hubel, C., et al., Am. J. Obstet Gynecol. 1996; 174:975–82.

Elevated levels of lipoprotein(a) in women with preeclampsia, Wang, J., et al., Am. J. Obstet Gynecol. 1998; 178:146–9.

Increased lipolytic activity and high ratio of free fatty acids to albumin in sera from women with preeclampsia leads to triglyceride accumulation in cultured endothetial cells, Endresen, M., et al., Am. J. Obstet Gynecol, 1992; 167:440–7.

Serum from preeclamptic women induces vascular cell adhesion molecule–1 expression on human endothelial cells in vitro: A possible role of increased circulating levels of free fatty acids, Endresen, M., et al., Am. J. Obstet Gynecol. 1998; 179:665–70.

Plasma type II phospholipase $A_2$ levels are elevated in severe preeclampsia, Lim, K., et al., Am. J. Obstet Gynecol. 1995; 172:998–1002.

Plasma cellular fibronectin as a measure of endothelial involvement in preeclampsia and intrauterine growth retardation, Friedman, S., et al., Am J. Obstet Gynecol, 1994; 170:838–41.

Growth factor activity in the blood of women in whom preeclampsia develops is elevated from early pregnancy, Taylor, R., et al., Am. J. Obstet Gynecol. 1990; 163:1839–44.

Prevention of preeclampsia: A big disappointment, Sibai, B., Am. J. Obstet Gynecol. 1998; 179:1275–8.

Trial of Calcium to Prevent Preeclampsia, Levine R., et al., N. Engl. J. Med. 1997; 337:69–76.

Prevention or Early Treatment of Preeclampsia, Roberts, J., N. Engl. J. Med. 1997; 337:124–5.

Is oxidative stress the link in the two–stage model of pre–eclampsia?, Roberts, J., et al., Lancet 1999; 354:788–9.

Preterm birth and pre–eclampsia—bad news and good news, Roberts, J., et al., Lancet 1998; 352 (suppl IV): 22.

Regulation of Human Placental Development by Oxygen Tension, Genbacev, O., et al., Science 1997; 277:1669–72.

Preeclampsia Is Associated with Failure of Human Cytotrophoblasts to Mimic a Vascular Adhesion Phenotype, Zhou, Y., et al., J. Clin. Invest. 1997; 99:2152–2164.

(List continued on next page.)

Primary Examiner—Ralph Gitomer
Assistant Examiner—Mahreen Chaudhry
(74) Attorney, Agent, or Firm—Lyon & Lyon LLP

(57) ABSTRACT

The present invention relates generally to methods for detecting preeclampsia in pregnancies. The present invention comprises the steps of obtaining a sample specimen from a patient, assaying the specimen to determine the level of glycerophosphatidyl compounds, glycerophosphatidylcholine, lysophospholipids and/or lysophosphatidylcholine in the sample, comparing levels in the sample to levels in normal samples, and correlating significant decreases as compared to normal samples as a positive indicator of preeclampsia.

16 Claims, 4 Drawing Sheets

OTHER PUBLICATIONS

Human Cytotrophoblasts Adopt a Vascular Phenotype as They Differentiate, Zhou, Y., et al., J. Clin. Invest. 1997; 99:2139–2151.

Hypoxia Alters Early Gestation Human Cytotrophoblast Differentiation/Invasion In Vitro and Models the Placental Defects that Occur in Preeclampsia, Genbacev, O., et al., J. Clin. Invest. 1996; 97:540–550.

Pregnancy–Induced Hypertension in Nulliparas Increases Morbidity but Not Mortality, Hauth, J., Obstet. Gynecol. 2000; 95:24–28.

Adeza Product Information.

* cited by examiner-

DETERMINING EXISTENCE OF PREECLAMPSIA IN PREGNANCIES BY MEASURING LEVELS OF GLYCEROPHOSPHATIDYL COMPOUNDS, GLYCEROPHOSPHATIDYCHOLINE, LYSOPHOSPHOLIPIDS AND LYSOPHOSPHATIDYLCHOLINE

FIELD OF INVENTION

The present invention relates to methods for the early detection of complications in pregnancy based on the detection of bioactive lipids. Specifically, the present invention relates to methods for early detection of preeclampsia and related disorders by detecting levels of glycerophosphatidyl compounds and lysophospholipids in a sample specimen obtained from a pregnant woman.

BACKGROUND

Preeclampsia is a condition responsible for up to 50–70% of hypertensive. complications in pregnancies. Although a leading cause of morbidity and mortality in pregnancies, its etiology and causes remain largely unknown. In severe cases, preeclampsia may develop into eclampsia, which often leads to death. Despite the dangers associated with preeclampsia, no cure exists for preeclampsia, although early detection and diagnosis enables therapy and treatment protocols that offer the best chance to save the lives of the baby and the mother.

Preeclampsia generally occurs after the $20^{th}$ week of pregnancy and appears without much warning. The most common symptoms are high blood pressure, swelling or edema of hands and feet, and increased protein in the urine. In the United States, preeclampsia is responsible for up to 10% of pregnancy-related mortality and morbidity each year. Preeclampsia is more prevalent in women under 20 or over 40 years of age. Those with pre-existing existing conditions of diabetes mellitus, renal diseases, high blood pressure, family history of preeclampsia, or previous complications with preeclampsia, are often at increased risk.

Although preeclampsia usually occurs during the second half of pregnancy, placental abnormalities related to preeclampsia appear early in the pregnancy. In normal pregnancies, a certain type of cells, known as cytotrophoblast stem cells, invade the uterus to help exchange nutrients and oxygen between the mother and the fetus. In preeclamptic patients, cytotrophoblast stem cells develop abnormally and invade into the placenta only shallowly. This shallow invasion prevents adequate blood flow to the placenta and deprives normal oxygen and food flow to the fetus. Babies born to preeclamptic women are often underweight due to inadequate nutrition and availability of oxygen.

Depending on the severity of the condition, preeclampsia varies from mild to severe. Mild preeclampsia is characterized by blood pressure readings of about 140/90 mm Hg, less than 5 g of protein in the urine a day, and swelling of face and hands. More severe forms of preeclampsia are characterized by blood pressure readings of about 160/110 mm Hg, over 5 g of protein in the urine a day, and beginning signs of end organ damage. Headaches, upper abdominal pains, impaired vision, fever, and vomiting are additional symptoms of preeclampsia. In extreme cases, preeclampsia can develop into eclampsia, which may lead to death and is characterized by seizure and coma.

Despite early treatment of mothers diagnosed with preeclampsia with aspirin and calcium, recent research has proven these treatment methods to be disappointing. To minimize risks to both mother and fetus, early detection is one of the most important factors in providing timely medical supervision and adequate expert care. In order to ensure that each case is detected at the earliest possible stage, it is also necessary to screen all mothers who are at risk for developing preeclampsia. Thus, a pressing need exists for an accurate, easy and cost effective method of detecting preeclampsia.

SUMMARY OF INVENTION

The present invention relates generally to methods for detecting preeclampsia in pregnancies. Specifically, the present invention comprises the steps of obtaining a sample specimen from a patient, assaying the specimen to determine the level of glycerophosphatidyl compounds, glycerophosphatidylcholine, lysophospholipids and/or lysophosphatidylcholine in the sample, comparing levels in the sample to levels in normal samples, and correlating significant changes as compared to normal samples as a positive indicator of preeclampsia.

In a preferred embodiment of the diagnostic method of the invention, the total amount of lysophospholipids (LPX) in a sample is measured by conversion into glycerol-3-phosphate (G3P). In an especially preferred embodiment, the sample specimen is incubated with lysophospholipase and a non-specific glycerophsphoryl compound phosphodiesterase to produce G3P from LPX. Then, the concentration of G3P thus produced is thereafter determined using an enzymatic cycling reaction.

In another preferred embodiment of the diagnostic method of the invention, the total amount of glycerophosphatidyl compounds (GPX) in a sample is measured by conversion into glycerol-3-phosphate (G3P). In an especially preferred embodiment, the sample specimen is incubated with a non-specific glycerophsphoryl compound phosphodiesterase to produce G3P from LPX. Then, the concentration of G3P thus produced is thereafter determined using an enzymatic cycling reaction.

In another preferred embodiment of the invention, the amount of lysophosphatidylcholine (LPC) in the sample is measured by enzymatically liberating choline from GPC. In especially preferred embodiments, samples are incubated with lysophospholipase and glycerophosphorylcholine phosphodiesterase to liberate choline from LPC. Choline is then preferably quantified using choline oxidase in a colorimetric reaction.

In another preferred embodiment of the invention, the amount of glycerophosphatidylcholine (GPC) in the sample is measured by enzymatically liberating choline from GPC. In especially preferred embodiments, samples are incubated with glycerophosphorylcholine phosphodiesterase to liberate choline from GPC. Choline is then preferably quantified using choline oxidase in a calorimetric reaction.

In yet another preferred embodiment of the invention, the amounts of at least two markers in the sample are measured, wherein the markers are chosen from the group consisting of glycerophosphatidyl compounds, glycerophosphatidylcholine, lysophospholipids, and lysophosphatidylcholine.

Another aspect of the present invention concerns diagnostic kits for the determination of preeclampsia in pregnant patients according to the above claimed method. Preferred embodiments of the diagnostic kits include enzymes and reagents necessary for the determination of the level of total glycerophosphatidyl compounds, glycerophosphatidylcholine, lysophospholipids and/or lysophosphatidylcholine in a specimen obtained from a pregnant patient, and instructions for making a preeclamptic diagnosis utilizing the kit. It is also preferred that the kit contain normal GPX, GPC, LPX or LPC level standards for comparison to the specimen obtained from the patient.

DETAILED DESCRIPTION

Figure 1:
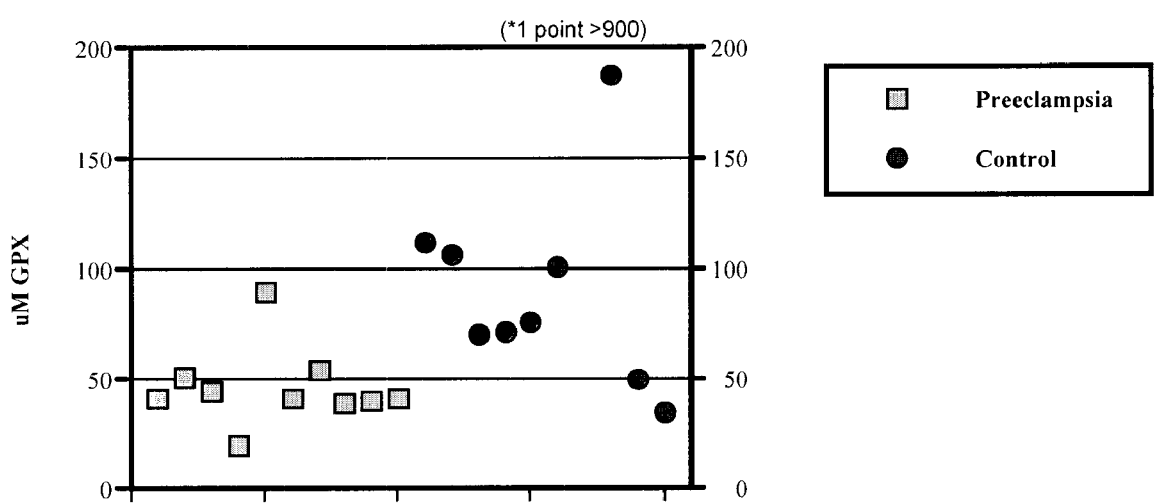
FIG. 1: A histogram of the GPX data shown in Table 1. The ● data points are control patients; the □ data points are preeclamptic patients.

The present invention provides a simple, accurate, and minimally invasive method for detecting preeclampsia in early pregnancies. Generally, the methods of the invention comprise obtaining a specimen from a pregnant patient, assaying the specimen to determine the level of glycerophosphatidyl compounds (GPX), glycerophosphatidylcholine (GPC), lysophospholipids (LPX) and/or lysophosphatidylcholine (LPC) in the specimen, and comparing the measured level with normal levels from non-preeclamptic specimens. Lower than normal levels of GPX, GPC, LPX and/or LPC signal the existence of a preeclamptic condition in the patient. Glycerophosphatidyl compounds, as the term is used in the present invention, include glycerol-3-phoaphate (G3P), glycerophosphatidylinositol (GPI), glycerophosphatidylcholine (GPC), glycerophosphatidylserine (GPS), glycerophosphatidylglycerol (GPG), and glycerophosphatidylethanolamine (GPE).

The present invention is advantageous in that it provides a more rapid and sensitive method for detecting preeclampsia. Small amounts of glycerophosphatidyl compounds and bioactive lipids, specifically lysophospholipids and lysophosphatidylcholine, are detected in the sample accurately and reliably to determine the existence of preeclamptic conditions. The present invention may be used throughout the various stages of pregnancy. Preferably, preeclampsia is detected during the first trimester of pregnancy in order to start therapeutic interventions as early as possible. However, the methods of the invention may also be used to detect preeclampsia in the second or third trimester of pregnancy. The present invention is also minimally invasive and cost efficient. Prepackaged diagnostic kits for measuring levels of glycerophosphatidyl compounds, glycerophosphatidylcholine, lysophospholipids and lysophosphatidylcholine in specimens from pregnant patients, as described below, can easily be used by clinicians for widespread screening of pregnant patients for preeclampsia. Thus, the present invention provides an easily administered test for a major health threat to pregnant women.

Different types of specimens, including plasma, serum, and urine, may be used in the claimed methods for detecting preeclampsia. Anti-coagulants such as heparin and chelating agents are usually added to whole blood specimen to minimize the activation of platelets and to reduce endogenous enzymatic activity. In obtaining a serum specimen, whole blood is preferably centrifuged by standard procedures at 500×g for 3 minutes or up to 3000×g for 15 minutes. A plasma sample is typically obtained by centrifugation. The blood sample is centrifuged at preferred speeds of between 400 to 1000×g to pellet out the blood cells, and the resulting supernatant is collected. Higher speeds of 2000 to 3000×g may also be used to more thoroughly pellet out the platelets. Further, urine specimens may be collected under conventional conditions.

Depending on the type of specimen and preparation procedure employed, the particular level of GPX, GPC, LPX and/or LPC indicative of preeclampsia may vary. An ordinarily skilled artisan would be able of determine the appropriate levels to differentiate between normal and preeclamptic levels of GPX, GPC, LPX or LPC in each of the different specimen types using routine experimentation as guided by the specification and the examples below. Initially, normal and preeclamptic levels of GPX, GPC, LPX and LPC are determined using non-preeclamptic samples for the type of specimen, as has been done for plasma samples in Examples 1 and 2. By analyzing this data, one of ordinary skill in the art may determine the particular concentration of lysophospholipid in a sample type which signals a significant decrease in levels of GPX, GPC, LPX and LPC in the sample as compared to normal levels of the same sample type. Then, this data analysis may be used for comparison with a specimen obtained from a patient to determine whether the level of GPX, GPC, LPX or LPC in the specimen is significantly lower than normal, or indicative of a preeclampsia.

In addition, combinations of GPX, GPC, LPX and LPC are simultaneously assayed in a sample from a patient, and the levels of these molecules are used in conjunction to arrive at a diagnosis of preeclamptic pregnancy. As is evident in the data presented in Tables 1 and 2, normal patients present a wide range of GPX, GPC, LPX and LPC levels, although preeclamptic patients present levels which are more consistently low. By manipulating the data obtained from assessing GPX, GPC, LPX and LPC, a practitioner in the medical diagnostic arts can devise combination tests utilizing these data which will eliminate some of the normal variance in individual GPX, GPC, LPX and LPC levels and allow for a better separation of non-preeclamptic from preeclamptic patients. For instance, assaying combined GPX+LPX levels may allow one to distinguish non-preeclamptic patients from preeclamptic patients (by generating fewer "false positives" below the preeclamptic indication level) better than assaying patients for GPX or LPX alone. An added benefit to such combined level analyses is that a one well reaction which cleaves both LPX and GPX (or LPC and GPC) may be used, rather than the two wells which are necessary to measure LPX and GPX (or LPC and GPC) separately, as described below.

In an alternative embodiment of the present invention, an individual is tested repeatedly over time to monitor for any significant changes. A significant change such as a decrease in GPX, GPC, LPX or LPC concentrations as compared to previous levels in a specimen from the patient may signal the onset of preeclampsia, or further deterioration of the preeclamptic condition. In contrast, increases in levels of GPX, GPC, LPX or LPC closer to normal levels may signal an improvement in the condition.

Preferably, the level of lysophospholipid, lysophosphatidylcholine, glycerophosphatidyl compounds, glycerophosphatidylcholine, or other markers are compared to a control value that is representative of normal levels of any or all of the above compounds obtained from non-preeclamptic patients. In practice, the control value may be a simple numerical reference value that is based on a population of samples reflecting a normal physiology that has been provided with the assay of the present invention for comparative purposes such that a comparison to the assay value can be made and the differential used to assess the preeclamptic condition. Alternatively, the control value may be obtained by performing the assay in duplicate with a control that contains one or more predetermined concentration or concentrations (i.e. to determine linearity) of any of the above-described compounds. In certain assay systems, the control value may be a calibration standard obtained from a control solution. In the embodiment of the invention where the patient's preeclamptic condition is monitored over time, the control value may comprise, or be compared to, a reading from the same patient under a different condition, particularly at a different point in time. With this approach, the preeclamptic condition can be monitored over a period of time by obtaining a series of samples and measurements for comparison both with control value(s) and with previous measurements.

Preferred embodiments for determining levels of LPX and LPC in sample specimen are discussed in detail below. The specification of U.S. Pat. No, 6,255,063, ENZYME METHOD FOR DETECTING LYSOPHOSPHOLIPIDS AND PHOSPHOLIPIDS AND FOR DETECTING AND CORRELATING CONDITIONS ASSOCIATED WITH ALTERED LEVELS OF LYSOPHOSPHOLIPIDS, issued Jul. 3, 2001, which is instructive for teaching methods of measuring LPX and LPC levels, is incorporated fully herein by reference. In addition, the specification of U.S. application Ser. No. 09/558,880, METHOD OF DETECTING CARCINOMAS, filed Apr. 26, 2000, which is instructive for teaching methods of measuring GPX and GPC levels, is also incorporated fully herein by reference.

A preferred method for measuring GPX and LPX in the specimen generally comprises converting GPX or LPX into G3P and assaying for the concentration of G3P produced in the sample. A portion of the specimen, which has not been enzymatically converted, may also be assayed for the concentration of endogenous, or "background" G3P. Otherwise, the level of all glycerophosphatidyl compounds is measured after conversion of GPX to G3P. Thus, the amount of G3P produced by the enzymatic cleavage of LPX may be determined by subtracting the level of "background" G3P and G3P produced from GPX from the G3P detected in the phospholipase cleaved sample.

To convert LPX into G3P, lysophospholipase is used in the enzymatic reaction to cleave the fatty acid group from the G3P and other glycerophosphatidyl compound (GPX) backbones. GPX is preferably digested using glycerophosphatidyl compound phosphodiesterase (GPX-PDE) to cleave the substituent from the phosphate of the G3P backbone. Thus, the amount of G3P produced by both of these enzymatic cleavage reactions is directly proportional to the total amount of LPX in the specimen, and the amount of G3P produced from GPX-PDE cleavage alone is directly proportional to the amount of GPX in the sample.

The amount of G3P in the cleaved and uncleaved portions of the sample specimen is then quantified using conventional or enzymatic techniques. If the size of the blood specimen is 2 ml or less, a quantification technique capable of detecting picomole amounts of the glycero compound may be used. Suitable conventional techniques for detecting picomole amounts include mass spectrometry.

Another preferred technique for determining the amount of G3P in the samples is an enzymatic cycling reaction. Specifically, an enzyme cycling reaction using glycerol-3-phosphate dehydrogenase (GDH), glycerol-3-phosphate oxidase (GPO) and NADH is used to accumulate $H_2O_2$ and NAD (U.S. Pat. No. 5,122,454, Ueda et al.). In the reaction, G3P is converted into dihydroxyacetone phosphate (DAP) and $H_2O_2$ using GPO in the presence of oxygen and water. In the presence of DAP, G3P dehydrogenase converts dihydroxyacetone phosphate back to G3P and oxidizes NADH to NAD.

The disappearance of NADH is monitored spectrophotometrically preferably at $OD_{340}$. In alternative embodiments, $H_2O_2$ production may be measured by colorimetry, fluorometry, or chemiluminescence. For the colorimetric assay, any of a number of chromogenic substrates, such as 4-aminoantipyrine (AAP), pyrogallol, 2-($2^1$-Azinobis (3-ethylbenzthiazoline-sulfonic acid)(ABTS) and 3,$3^1$,5,$5^1$-tetramethylbenzidine) (TMB), may be used. Numerical values are obtained from a standard curve consisting of known concentrations of G3P, and assays are preferably performed in duplicate with both positive and negative controls. The difference between $OD_{340}$ or $OD_{505}$ before and after the enzyme cycling reaction is directly proportional to the amount of G3P present. Background signals in the specimen without the cycling enzyme mix are subtracted from all samples, and G3P standard curve values are plotted and fitted to a linear or second-order polynomial curve fit. The levels of G3P in each sample are determined by comparing each signal measured to the standard curve. Finally, the level of G3P attributable to LPX is determined by subtracting out the GPX measurement. Optionally, one can determined the level of substituted glycerophosphatidyl compounds (GPC, GPI, GPE, GPG, GPS) by subtracting out the G3P level detected in a portion of the sample which has not been digested with a phospholipase or GPX-PDE.

Although the level of glycerophosphatidylcholine and lysophosphatidyleholine may be determined by as above by first separating LPC and GPC from the total lysophospholipid in the sample, in a preferred embodiment for determining the concentration of LPC and GPC, choline is measured after being liberated from GPC and LPC. Glycerophosphorylcholine and fatty acid are first liberated from LPC using phospholipase B or lysophospholipase. The level of LPC is then determined by liberating choline and glycero-3-phosphate (G3P) from glycerophosphorylcholine using glycerophosphorylcholine phosphodiesterase (GPC-PDE), followed by a calorimetric enzymatic determination of choline using choline oxidase, 4-aminoantipyrine (AAP), 3,5 Dichloro-2-hydroxybenzenesulfonic acid sodium salt (HDCBS) and peroxidase. The background level of glycerophosphorylcholine and choline is determined by measuring the glycerophosphorylcholine and choline in a portion of the sample which has not been enzymatically treated with phospholipase to cleave LPC. Although the background level of endogenous choline may be determined by performing the choline oxidase reaction in a portion of the sample which has not been digested with a phospholipase or GPC-PDE, the amount of endogenous choline in a sample was not significant in the applicant's experience.

Choline is preferably detected by oxidizing to $H_2O_2$ and betaine and using peroxidase to form quinoneimine dye. Alternatively, G3P is measured using G3P dehydrogenase and oxidase in the cycling reaction as described above. After comparison to a standard curve, the level of LPC in the sample is determined by subtracting the background level of glycerophosphorylcholine and choline from the level of choline determined in the phospholipase cleaved portion of the sample.

To optimize detection of lysophospholipids, inhibitors may be used to prevent degradation of the glycerophosphatidyl compounds and lysophospholipids in the sample. Such inhibitors include phosphodiesterase inhibitors such as IBMX (3-Isobutyl-1-methylxanthine, CalBiochem, La Jolla, CA); Ro-20-1724 (CalBiochem); Zaprinast (CalBiochem) and Pentoxifylline (CalBiochem); general protease inhibitors such as E-64 (trans-Epoxysuccinyl-L-leucylamido-(4-guanidino)butane, Sigma); leupeptin (Sigma); pepstatin A (Sigma); TPCK (N-tosyl-L-phenylalanine chloromethyl ketone, Sigma); PMSF (Phenylmethanesulfonyl fluoride, Sigma); benzamidine (Sigma) and 1, 10-phenanthroline (Sigma); organic solvents including chloroform and methanol; detergents such as SDS or Trident X100; proteases that would degrade phospholipases such as trypsin (Sigma) and thermostable protease (Boehringer Mannheim Biochemicals, Indianapolis, IN); and metal chelators such as EDTA (Ethylenediaminetetracetic acid, Sigma) and EGTA (Ethylene glycol-bis-(beta-aminoethyl ether), Sigma). In some embodiments, $MgCl_2$ and/or EDTA were included in the assay buffers to optimally determine levels of each analyte.

In a preferred embodiment, microtiter plates may be used for small volumes of samples and reagents. An ELISA reader may also be used to monitor and help automate the assay, and the reduced processing times may in turn reduce variability between results. The methods of the present invention may further be easily adapted for use in microscale automated assay equipment, such as the Immuno I system available from Bayer, the Access system available from Beckman Coulter, or the Dimension RxL HM system available from Dade Behring.

The present invention also contemplates convenient pre-packaged diagnostic kits for detecting levels of GPX, GPC, LPX and/or LPC. Preferably, these kits contain enzymes and reagents necessary for determining the level of GPX,-GPC, LPX and/or LPC as described above. For example, diagnostic kits preferably include enzymes and buffers for the cleavage of GPX, GPC, LPX and LPC. Exemplary enzymes for inclusion in such kits are phospholipase B, lysophospholipase, glycerophosphitidyl compound phosphodiesterase, and glycerophosphatidylcholine phosphodiesterase. In addition, the kits of the present invention preferably include reagents for determining concentrations of G3P, including enzymatic cycling reaction reagents such as glycerol-3-phosphase dehydrogenase, glycerol-3-phosphate oxidase, NADH and other ancillary agents such as buffering agents, colorimetric reagents for the detection of peroxide generation, and EDTA.

Optionally, the kits may include reagents necessary to separate GPC or LPC from the other lysophospholipids in the sample. Preferably, the kits of the present invention include reagents for measuring choline liberated from GPC or LPC in the specimen. Such reagents may include, for example, choline oxidase, peroxidase, 4-aminoantipyrine (AAP), 3,5 Dichloro-2-hydroxybenzenesulfonic acid sodium salt (HDCBS), and other ancillary agents such as buffering agents.

The kits of the invention also comprise containers and appropriate instructions for carrying out the inventive method. Preferred embodiments of the kits of the invention also include standards for comparison with the specimens obtained from the patients, in order to assure that the clinician has properly performed the claimed method while using the kit. Variations of specific container and combination embodiments of the kits of the invention may readily be devised by those of ordinary skill in the art utilizing the guidance herein provided.

The present invention is further described in the following examples. These examples do not, in any way, limit the present invention.

EXAMPLES

Example 1

Assay of Plasma Specimen Levels of Lysophospholipid (LPX) and Glycerophosphatidyl Compounds (GPX) as Measured by Levels of G3P for the Detection of Preeclampsia Plasma samples were obtained from blood specimen provided by twenty female patients. A whole blood specimen was collected from each of the patients in a vacutainer tube containing EDTA. The whole blood specimen was then centrifuged under standard conditions to provide a pellet of the blood cells and platelets and a supernatant. The plasma supernatant was either processed immediately or stored at $-70°$ C.

Reagents

Lysophospholipase (LYPL) was purchased from Asahi Chemical Industry, Tokyo, Japan. Glycerol-3-phosphate oxidase, glycerol-3-phosphate dehydrogenase, human plasma, human serum, 4-aminoantipyrine (AAP), and glycerophosphorylcholine phosphodiesterase (GPX-PDE) were purchase from Sigma Chemical Co., St. Louis, Mo. Peroxidase and NADH were purchased from Boehringer Mannheim, Indianapolis, Ind. All lipid or glycerophosphatidyl standards were purchased from Avanti Polar Lipids, Alabaster, AL or Sigma Chemical Co.

Enzyme Assay

Using a 96 well microtiter plate, 5 $\mu$l of the diluted sample were aliquotted into pairs of wells. To one well of each pair, the "LPX+GPX" well, 100 $\mu$l of LYPL (0.05 Units)/GPC-PDE (0.0125 Units) were added. 100 $\mu$l of GPC-PDE (0.0125 Units) were added to the other "background GPX" well. The wells were then incubated at 37° C. for 15 minutes. Glycerophosphatidyl compounds were produced as an intermediate by LYPL digestion of LPX. G3P and the phosphoryl substituents were then liberated from the glycerophosphatidyl compounds using GPX-PDE. G3P levels were then determined by enzymatic assay of the plasma samples. 100 $\mu$L of cycling reaction enzyme mix containing 10 units of G3P dehydrogenase, 4 units of G3P 6oxidase, and 0.34 mM NADH in 50 mM Tris (pH 8.0) were added to each well, and incubated at 37° C. for 30 minutes. The G3P oxidase converts G3P to dihydroxyacetone phosphate and $H_2O_2$, and G3P dehydrogenase converts the dihydroxyacetone phosphate back into G3P. This reaction oxidizes NADH to NAD, and as cycling continues, both $H_2O_2$ and NAD accumulate.

The total amount of G3P was determined by monitoring the oxidation of NADH (i.e. the reduction of absorbance at 340 nm after the cycling action compared to $A_{340}$ before cycling). In addition, the accumulation of $H_2O_2$ was determined calorimetrically by adding 50 $\mu$l of a solution containing 0.5 units peroxidase, 0.5% HDCBS and 0.15% AAP in 50 mM Tris 8.0 to each well and recording the absorbance at 505 nm.

Numerical values of G3P concentrations were obtained from a standard curve constructed from known G3P amounts. An internal standard of plasma was included within each assay (i.e. each plate) that was measured at different dilutions. In some cases, this internal standard was used to correct for variations between different experiments. When the calorimetric method was used, the plate was blanked at 505 nm prior to color development.

Figure 2:
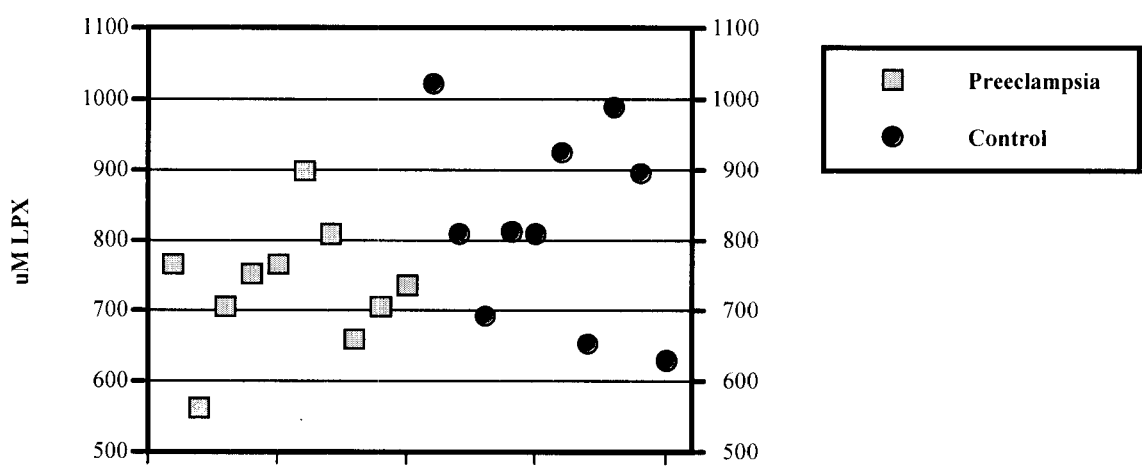
FIG. 2: A histogram of the LPX data shown in Table 1. The ● data points are control patients; the □ data points are preeclamptic patients.

The concentrations of LPX in each sample were determined by subtracting the "background GPX" well G3P level from the G3P level detected in the "LPX+GPX" well of as the samples. The concentrations in $\mu$M of GPX in each of the samples are presented in Table 1 and FIG. 1. The concentrations in $\mu$M of LPX in each of the samples are presented in Table 1 and FIG. 2. Preeclamptic blood samples were drawn from patients who were diagnosed with preeclampsia one week later. Normal blood samples, however, were drawn from patients who were not diagnosed with preeclampsia.

TABLE 1

| SAMPLE | DIAGNOSIS | GPX | LPX |
|--------|-----------|-----|-----|
| 1 | Preeclampsia | 42 | 766 |
| 2 | Preeclampsia | 51 | 562 |
| 3 | Preeclampsia | 45 | 706 |
| 4 | Preeclampsia | 20 | 753 |
| 5 | Preeclampsia | 90 | 767 |
| 6 | Preeclampsia | 41 | 898 |
| 7 | Preeclampsia | 55 | 808 |
| 8 | Preeclampsia | 39 | 660 |
| 9 | Preeclampsia | 40 | 707 |
| 10 | Preeclampsia | 41 | 737 |
| 11 | Control | 113 | 1024 |
| 12 | Control | 107 | 809 |
| 13 | Control | 70 | 693 |
| 14 | Control | 71 | 813 |
| 15 | Control | 76 | 809 |
| 16 | Control | 101 | 925 |
| 17 | Control | 921 | 654 |
| 18 | Control | 188 | 989 |
| 19 | Control | 50 | 895 |
| 20 | Control | 35 | 628 |

Control Sample 17 was clearly aberrant, and so was discarded from mean and standard deviation calculations by accepted statistical methodology. As noted in the above cited co-pending applications, such abnormally high levels of glycerophosphatidyl compounds are sometimes observed in patients with disease states unrelated to preeclamptic pregnancy. As shown in Table 1, lower than normal levels of LPX were found generally in patients later developing preeclampsia. The average concentration of LPX from preeclamptic samples measured 736.2±88.9 $\mu$M, whereas the average concentration of LPX in normal samples measured 842.7±130.1 $\mu$M. Concentrations of LPX in preeclamptic samples on average were 106 $\mu$M lower than concentrations in normal samples. Thus, the average concentration of LPX in the plasma of patients later developing preeclampsia was significantly lower than the average concentration of LPX in the plasma of healthy patients. Also shown in Table 1, lower than normal levels of GPX were found generally in patients later developing preeclampsia. The average concentration of GPX from preeclamptic samples measured 46.3±17.8 $\mu$M, whereas the average concentration of GPX in normal samples measured 90.2±44.8 $\mu$M. Concentrations of GPX in preeclamptic samples on average were 44 $\mu$M lower than concentrations in normal samples. Thus, the average concentration of GPX in the plasma of patients later developing preeclampsia was significantly lower than the average concentration of GPX in the plasma of healthy patients.

Example 2

Assay of Plasma Specimen Levels of Lysophosphatidylcholine (LPC) and Glycerophosphatidylcholine (GPC) as Measured by Levels of Choline for the Detection of Preeclampsia Reagents Lysophospholipase (LYPL) was purchased from Asahi Chemical Industry, Tokyo, Japan. Glycerophosphorylcholine phosphodiesterase (GPC-PDE), choline oxidase, and 4-aminoantipyrine (AAP) were purchased from Sigma Chemical Co., St. Louis, Mo. Peroxidase was purchased from Boerhinger Mannheim, Indianapolis, IN. 3,5 Dichloro-2-hydroxybenzenesulfonic acid sodium salt (HDCBS) was purchased from Biosynth AG, Naperville, Ill. All lipid and glycerophosphatidyl standards were purchased from Avanti Polar Lipids, Alabaster, AL or Sigma Chemical Co.

Sample Collection and Processing

Plasma was processed from blood collected as described in Example 1.

Enzymatic Assay

Figure 3:
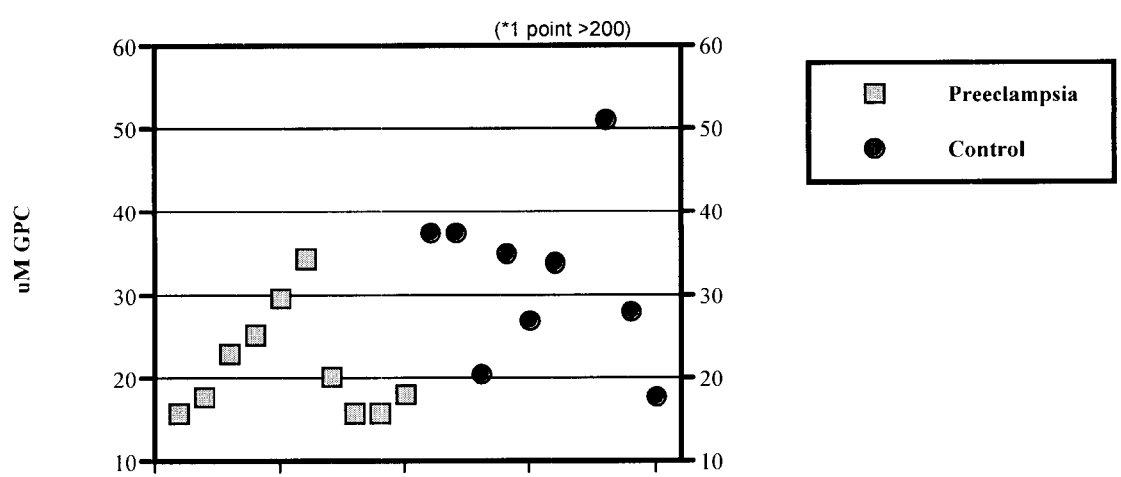
FIG. 3: A histogram of the GPC data shown in Table 2. The ● data points are control patients; the □ data points are preeclamptic patients.
Figure 4:
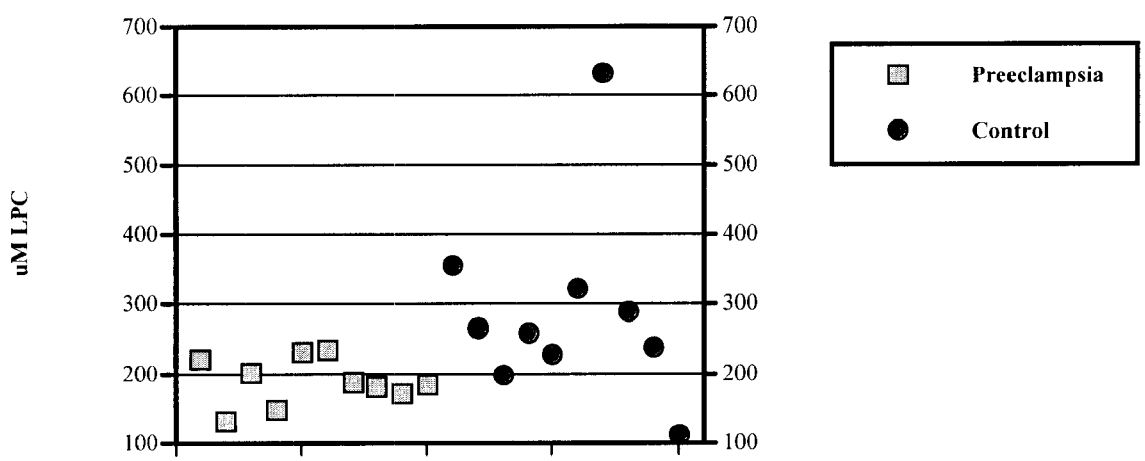
FIG. 4: A histogram of the LPC data shown in Table 2. The ● data points are control patients; the □ data points are preeclamptic patients.

Using a 96 well microtiter plate, 5 $\mu$l of the sample were aliquotted into pairs of wells. To one well of each pair, the "LPC+GPC" well, 100 $\mu$l of LYPL (0.05 Units)/GPC-PDE (0.0125 Units) were added. 100 $\mu$l of GPC-PDE (0.0125 Units) were added to the other "background GPC" well. The wells were incubated at 37° C. for 15 minutes. Glycerophosphorylcholine was produced as an intermediate by LYPL digestion of LPC. G3P and choline were then liberated from glycerophosphorylcholine using GPD-PDE. The plate was then blanked A505 in the ELISA reader, and 50 $\mu$l choline detection mix (0.15 Units choline oxidase, 0.5 Units peroxidase, 0.03% AAP, 0.125% HDCBS, 100 mM Tris pH 8.0) were added and incubated at 37° C. for 15 minutes. The plate was then read at $A_{505}$. The concentrations of LPC in each sample were determined by subtracting the "background" glycerophosphatidylcholine and choline levels from the choline level in the cleaved portions of the samples. TABLE 2 and FIG. 3 illustrate the results of the assay for GPC. TABLE 2 and FIG. 4 illustrate the results of the assay for LPC.

TABLE 2

| SAMPLE | DIAGNOSIS | GPC | LPC |
|--------|-----------|-----|-----|
| 1 | Preeclampsia | 15.85 | 224 |
| 2 | Preeclampsia | 17.83 | 134 |
| 3 | Preeclampsia | 23.24 | 203 |
| 4 | Preeclampsia | 25.27 | 151 |
| 5 | Preeclampsia | 29.91 | 232 |
| 6 | Preeclampsia | 34.55 | 235 |
| 7 | Preeclampsia | 20.26 | 190 |
| 8 | Preeclampsia | 15.96 | 182 |
| 9 | Preeclampsia | 15.85 | 172 |
| 10 | Preeclampsia | 18.05 | 185 |
| 11 | Control | 37.46 | 355 |
| 12 | Control | 37.55 | 267 |

TABLE 2-continued

| SAMPLE | DIAGNOSIS | GPC | LPC |
|---|---|---|---|
| 13 | Control | 20.59 | 198 |
| 14 | Control | 35.00 | 261 |
| 15 | Control | 27.09 | 231 |
| 16 | Control | 33.91 | 323 |
| 17 | Control | 208.59 | 632 |
| 18 | Control | 51.30 | 290 |
| 19 | Control | 28.27 | 238 |
| 20 | Control | 17.94 | 113 |

Control Sample 17 was clearly aberrant, and so was discarded from mean and standard deviation calculations by accepted statistical methodology. As noted in the above cited co-pending applications, such abnormally high levels of glycerophosphatidyl compounds are sometimes observed in patients with disease states unrelated to preeclamptic pregnancy. As seen in Table 2, lower than normal levels of LPC were generally found in patients later developing preeclampsia. Concentrations of LPC in patients with preeclampsia averaged 190.8±33.7 $\mu$M, whereas concentrations of LPC in normal patients average 252.9±71.1 $\mu$M. Thus, the average concentration of LPC in the plasma of patients diagnosed as having preeclampsia was significantly lower, by 62 $\mu$M, than the average concentration of LPC in the plasma of healthy patients. Also seen in Table 2, lower than normal levels of GPC were generally found in patients later developing preeclampsia. Concentrations of GPC in patients with preeclampsia averaged 21.7±6.5 $\mu$M, whereas concentrations of GPC in normal patients averaged 32.1±10.1 $\mu$M. Thus, the average concentration of GPC in the plasma of patients diagnosed as having preeclampsia was significantly lower, by 10 $\mu$M, than the average concentration of GPC in the plasma of healthy patients.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims.

I claim:

1. A method for detecting preeclampsia in pregnancy comprising:
   obtaining a sample specimen from a patient;
   assaying the sample specimen to determine the level of glycerophosphatidyl compounds in the specimen;
   comparing the level of glycerophosphatidyl compounds in the specimen to a control value; and
   correlating a lower level in the specimen to preeclampsia.

2. The method of claim 1, wherein the specimen is serum.

3. The method of claim 1, wherein the specimen is plasma.

4. The method of claim 1, wherein the specimen is urine.

5. The method of claim 1, wherein the step of assaying the sample specimen to determine the level of glycerophosphatidyl compounds in the sample further comprises:
   converting substituted glycerophosphatidyl compounds into glycero-3-phosphate by incubating with a non-specific glycerophosphoryl compound diesterase; and
   determining the total concentration of G3P using an enzymatic cycling reaction.

6. The method of claim 1, wherein the assaying step is repeated with a plurality of samples from the patient to monitor the condition.

7. A method for detecting preeclampsia comprising:
   obtaining a sample specimen from the patient;
   assaying the sample specimen to determine the level of glycerophosphatidylcholine in the specimen;
   comparing the level of glycerophosphatidylcholine in the specimen to a control value; and
   correlating a lower level in the specimen to preeclampsia.

8. The method of claim 7, wherein the specimen is serum.

9. The method of claim 7, wherein the specimen is plasma.

10. The method of claim 7, wherein the specimen is urine.

11. The method of claim 7, wherein the step of assaying the sample specimen to determine the level of glycerophosphatidylcholine in the sample further comprises:
    enzymatically liberating choline from glycerophosphatidylcholine with glycerophosphorylcholine phosphodiesterase; and
    determining the total concentration of choline in a colorimetric reaction utilizing choline oxidase.

12. The method of claim 7, wherein the assaying step is repeated with a plurality of samples from the patient to monitor the condition.

13. A pre-packaged diagnostic kit for detecting a preeclampsia comprising:
    a non-specific glycerophosphatidyl compound phosphodiesterase;
    glycerol-3-phosphate oxidase;
    glycerol-3-phosphate dehydrogenase; and
    a kit package and instructions.

14. The pre-packaged diagnostic kit of claim 13, further comprising a glycerophosphatidyl compound standard.

15. A pre-packaged diagnostic kit for detecting preeclampsia comprising:
    a glycerophosphatidylcholine phosphodiesterase;
    choline oxidase;
    peroxidase; and
    a kit package and instructions.

16. The pre-packaged diagnostic kit of claim 15, further comprising a glycerophosphatidylcholine standard.

* * * * *